United States Patent [19]

Kaminsky et al.

[11] Patent Number: 5,599,510
[45] Date of Patent: *Feb. 4, 1997

[54] CATALYTIC WALL REACTORS AND USE OF CATALYTIC WALL REACTORS FOR METHANE COUPLING AND HYDROCARBON CRACKING REACTIONS

[75] Inventors: Mark P. Kaminsky, Winfield; George A. Huff, Jr., Naperville; Narasimhan Calamur, Willowbrook; Michael J. Spangler, Sandwich, all of Ill.

[73] Assignee: Amoco Corporation, Chicago, Ill.

[*] Notice: The term of this patent shall not extend beyond the expiration date of Pat. No. 5,254,781.

[21] Appl. No.: 447,434

[22] Filed: May 23, 1995

Related U.S. Application Data

[63] Continuation of Ser. No. 107,912, Aug. 17, 1993, which is a continuation-in-part of Ser. No. 815,244, Dec. 31, 1991, Pat. No. 5,254,781.

[51] Int. Cl.$^6$ .................................................... C07C 2/00
[52] U.S. Cl. ............................ 422/197; 585/500; 585/602; 585/910; 585/911; 585/943
[58] Field of Search ..................... 422/188, 190, 422/192, 193, 191, 196, 197, 198, 202, 222; 585/500, 602, 910, 911, 943

[56] References Cited

U.S. PATENT DOCUMENTS

| | | | |
|---|---|---|---|
| 2,850,360 | 9/1958 | Bottenberg | 23/252 |
| 3,482,948 | 12/1969 | Miegel | 23/288 |
| 4,362,209 | 12/1982 | Cleveland | 165/166 |
| 4,926,001 | 5/1990 | Alagy et al. | 585/500 |
| 4,975,314 | 12/1990 | Yano et al. | 428/213 |
| 5,012,028 | 4/1991 | Gupta et al. | 585/500 |
| 5,093,298 | 3/1992 | Haddad et al. | 502/209 |
| 5,118,898 | 6/1992 | Tyler et al. | 585/500 |
| 5,254,781 | 10/1993 | Calamur et al. | 585/500 |
| 5,260,125 | 11/1993 | Copes | 428/285 |
| 5,356,728 | 10/1994 | Balachandran et al. | 429/8 |

OTHER PUBLICATIONS

Smith et al., *Chemical Engineering Science*, vol. 30, pp. 221–222 (1975).
Hatano et al., *Inorganica Chimica Acta.*, vol. 146, pp. 243–247 (1988).
Ungar et al., *Applied Catalysts*, vol. 42, pp. L1–L4 (1988).
Zhang et al., *J. Chem. Soc., Chem. Commun.*, pp. 473–475 (1989).

*Primary Examiner*—Robert J. Warden
*Assistant Examiner*—Robert Carpenter
*Attorney, Agent, or Firm*—Wallace L. Oliver; Frederick S. Jerome

[57] ABSTRACT

Dual-flow chemical reactor cores containing catalytic heat-transfer walls comprising both a gas-impervious material and a suitable catalyst which allows oxidative coupling of methane into higher hydrocarbons, dual-flow reactors having these catalytic heat-transfer walls to control and facilitate simultaneously coupling of methane and cracking of hydrocarbon compounds in separate gas streams, and chemical processes which combine coupling of methane and cracking of hydrocarbon compounds to make olefins in a dual-flow reactor having catalytic heat-transfer walls.

13 Claims, 4 Drawing Sheets

CATALYTIC WALL REACTORS AND USE OF CATALYTIC WALL REACTORS FOR METHANE COUPLING AND HYDROCARBON CRACKING REACTIONS

CROSS-REFERENCE TO RELATED APPLICATION

This application is a continuation of application Ser. No. 08/107,912 filed Aug. 17, 1993, which is a continuation-in-part of application Ser. No. 07/815,244 filed Dec. 31, 1991, now U.S. Pat. No. 5,254,781, issued Oct. 19, 1993, the specifications and claims of which are incorporated by reference herein.

TECHNICAL FIELD

This invention relates to chemical reactors useful to control simultaneously partial oxidation and pyrolysis reactions of different organic compounds to added-value products. In particular, this invention relates to dual-flow chemical reactors containing catalytic heat-transfer walls which have both gas-impervious materials and suitable catalysts allowing oxidative coupling of methane into higher hydrocarbons, and chemical processes using dual-flow reactors having such catalytic heat-transfer walls to control and facilitate transport of heat from methane coupling reactions in a methane-containing gas stream to cracking reactions of organic compounds in separate gas stream. These dual-flow reactors comprise either an array of tubes containing channels for flow of one gas stream positioned in another gas stream flow or a core containing channels for separated flow of a methane-containing gas stream and flow of organic compounds in another gas stream. Each channel has a portion of thermally conductive wall disposed between at least two different gas streams comprising a gas-impervious material and suitable catalyst for oxidative coupling of methane into higher hydrocarbons.

The invention includes reactors comprising first and second zones separated by catalytic heat-transfer walls which have both gas-impervious materials and suitable catalysts allowing oxidative coupling of methane into higher hydrocarbons. Preferred gas-impervious materials comprise high temperature metal alloys and/or non-metals materials including stainless steels, ceramics, silicon carbide, and the like.

The invention also includes a process for making olefins using a dual-flow reactor having catalytic heat-transfer wails to control and facilitate transport of heat from methane coupling reactions in a methane-containing gas stream to cracking reactions of organic compounds in another gas stream. This process combines the thermal and/or catalytic cracking of a hydrocarbon feed stock with the coupling of methane and allows separation of an enhanced amount of $C_2+$ products, and more particularly, to a process for making olefins in which a hydrocarbon feed is thermally cracked to form olefins in parallel with the catalytic coupling of methane to form largely $C_2$ hydrocarbons using an oxygen-affording gas, the methane coupling and cracking processes so arranged that the heat produced in the exothermic coupling reaction is effectively transferred to the endothermic cracking process, and in which the refrigeration required to liquefy air to produce oxygen for the methane coupling process is used to effect the cryogenic separation of the products contained in the effluent from the cracking process.

BACKGROUND OF INVENTION

It is well known that capacity of conventional reactors for chemical conversions of commercial interest is often heat transfer limited, because such chemical conversions are highly exothermic, endothermic, and/or require severe thermal conditions of reaction. For example, conventional fixed-bed and fluidized-bed catalytic reactors for exothermic gas phase reactions in which a catalytically active material is supported on or contained within solid particles, typically, have large gas-solid thermal resistance. In particular, one such technique is oxidative coupling of methane which involves reacting methane with oxygen over supported catalyst to produce higher hydrocarbons, principally ethane and ethylene, in fixed-bed and/or fluidized-bed catalytic reactors.

The commercial production of olefins including importantly ethylene, propylene and smaller amounts of butadiene and butylenes is generally accomplished by the thermal cracking using steam of ethane, propane or a hydrocarbon liquid ranging in boiling point from light straight run gasoline through gas oil. In a typical ethylene plant the cracking furnaces represent about 25% of the cost of the unit while the compression, heating, dehydration, recovery and refrigeration sections represent the remaining about 75% of the total. This endothermic process is carried out in large pyrolysis furnaces with the expenditure of large quantities of heat which is provided in part by burning the methane produced in the cracking process. After cracking, the reactor effluent is put through a series of separation steps involving cryogenic separation of products such as ethylene and propylene. The total energy requirements for the process are thus very large and ways to reduce it are of substantial commercial interest. In addition, it is of interest to reduce the amount of methane produced in the cracking process, or to utilize it other than for its fuel value.

More recently, because of the supply side pressure to find non-petroleum sources for industrial chemicals and the environmental need to reduce methane flaring from producing oil wells, natural gas, a source which is relatively abundant in the United States and other locations elsewhere in the world, has been investigated as a source of hydrocarbons and oxygenates. Various methods to convert the methane in natural gas to hydrocarbons have been suggested and some commercialized. Projects in New Zealand and at Sasol in South Africa are examples in which methane is converted to useful products. In New Zealand, methane is converted to a methanol and then to hydrocarbons, and in Sasol, methane is converted to synthesis gas and then to other products. Another such project is located in Malaysia.

Direct conversion of methane to major industrial intermediates such as ethylene and propylene has been the subject of much research in the past 10 years. While a number of catalysts and processes have been suggested for the conversion none, has yet been commercialized. One process which has been intensely researched is the high temperature methane coupling process using an oxygen-affording gas and a solid, metal oxide catalyst to form largely ethane and ethylene. Carbon dioxide formation which is favored thermodynamically is an undesired product in methane coupling as its formation uses carbon which is not readily available to form the desired hydrocarbons.

Pyrolysis processes are known which involve conversion of methane to higher molecular weight hydrocarbons at high temeratures, in excess of about 1200° C. These processes are, however energy intensive and have not been developed to the degree where high yields are obtained even with use of catalysts.

U.S. Pat. No. 4,507,517 and U.K. Patent Application GB 2,148,935A have taught catalytic processes for converting methane to $C_2+$ hydrocarbons, particularly hydrocarbons rich in ethylene and/or benzene, at temperatures greater than 1000° C. and gas hourly space velocities in excess of 3200 $hr^{-1}$. The U.S. patent used a boron containing catalyst. While the U.K. application disclosed a process which used a catalyst containing a metal compound of Groups IA, IIA, IIIA, IVB or Actinide Series of elements.

Catalytic oxidative coupling of methane at atmospheric pressure and temperatures in a range of from about 500° C. to about 1000° C. has been investigated by G. E. Keller and M. M. Bhasin. These researchers reported synthesis of ethylene via oxidative coupling of methane over a wide variety of metal oxides supported on an alpha alumina structure in *Journal of Catalysis*, 73, pages 9 to 19 (1982). They teach use of single component oxide catalysts that exhibited methane conversion to higher order hydrocarbons at rates no greater than 4%. The process used by Keller and Bhasin to oxidize methane was cyclic, varying the feed composition between methane, nitrogen and air (oxygen) to obtain higher selectivities.

U.S. Pat. Nos. 4,443,644; 4,443,645; 4,443,646; 4,443,647; 4,443,648,; 4,443,649; and 4,523,049 also disclose methods for converting methane to higher molecular weight hydrocarbons at temperatures in a range of about 500° C. to about 1000° C.

Low temperature pyrolysis of hydrocarbon feed stocks to higher molecular weight hydrocarbons at temperature in a range of about 250° C. to about 500° C. is reported in U.S. Pat. Nos. 4,433,192; 4,497,970; and 4,513,164. Processes described in these patents used heterogeneous systems and solid acid catalysts. In addition to the solid acid catalysts, the reaction mixtures described in latter two patents included oxidizing agents. Among the oxidizing agents disclosed are air, O2/O3 mixtures, S, Se, $SO_3$, $N_2O$, NO, $NO_3F$, and the like.

U.S. Pat. Nos. 4,172,810; 4,205,194; and 4,239,658 teach production of hydrocarbons including ethylene, ethane, propane, and benzene in the presence of a catalyst-reagent composition which comprises; (i) nickel, or a Group VIII metal or a Group IB having atomic number of 45 or greater; (ii) a Group VIB; and (iii) a preselected Group IIA metal; composted, for example, with a persisted, spinel-coated refectory support. Feed streams used in processes disclosed in these patents did not contain oxygen. Oxygen was avoided for the purposes of avoiding formation of coke in the catalyst. Oxygen was generated for reaction from the catalysts; thus periodic regeneration of these catalysts was required.

U.S. Pat. No. 4,450,310 teaches production of olefins and hydrogen from methane in the absence of oxygen and in the absence of water at reaction temperatures of at least 500° C. using catalyst comprising mixed oxides of a first metal selected from the group lithium, sodium, potassium, rubidium, cesium and mixtures thereof, a second metal selected from the group beryllium, magnesium, calcium, strontium, barium, and mixtures thereof, and optionally a promoter metal selected from the group copper, rhenium, tungsten, zirconium, rhodium, and mixtures thereof.

U.S. Pat. No. 4,560,821 discloses a continuous process for forming hydrocarbons from a source of methane by contacting methane with particles of catalyst wherein the particles circulate between two physically separate zones; a methane contact zone and an oxygen contact zone. In each zone the particles are maintained as fluidized beds of the solid particles. Useful catalysts are said to include reducible oxides of metals selected from the group Mn, Sn, In, Ge, Pb, Sb and Bi.

In U.S. Pat. No. 4,926,001, Institut Francais du Petrole (IFP) has taught a stem cracking process for thermal conversion of methane to hydrocarbons of higher molecular weights based on use of a multichannel system of ceramic material in which a methane feed passes through a pyrolysis zone followed by a quenching zone in a first set parallel rows of channels which are cooled by a cooling fluid passing through a second set of parallel rows of adjacent channels. Pyrolysis zone and following quenching zone are open to flow of methane and/or hydrocarbons directly from one zone to the another zone in the multichannel system described.

U.S. Pat. No. 5,012,028 discloses a continuous process for converting a gaseous reactant containing methane or natural gas to hydrocarbons wherein the gaseous reactant is contacted with an oxidative coupling catalyst in an oxidative coupling reactor at a reaction temperature in a range from 500° C. to 1100° C. to form an intermediate product, predominately ethane; and pyrolysis of an admixture of the intermediate product with a source other $C_2+$ gases in a pyrolysis reactor at a reaction temperature in a range from 900° C. to 1500° C. to form higher molecular weight hydrocarbon products. The total effluent from the oxidative coupling reactor or zone flows directly to the pyrolysis reactor or zone. Catalyst is supported on inert solid particles which are in the forms of fixed bed, fluid bed, spouted bed or monolith. External heat is, typically, applied to the pyrolysis reactor to supplement the heat provided with effluent from the oxidative coupling reactor.

Recently in U.S. Pat. No. 5,025,108, Institut Francais du Petrole (IFP) has taught a process for producing olefins from natural gas which involves pre-separation of the $C_2+$ components from the methane, catalytic oxidation of the methane to primarily ethane and ethylene, and the return of the $C_2+$ components to the effluent side of the methane coupling reaction where the saturated $C_2+$ components are then cracked to olefins. The process is said to effectively utilize the heat produced in the exothermic methane coupling to carry out the endothermic cracking process. The process has several drawbacks, however, including importantly the mixing of the carbon oxides and water components produced by the substantial amount of hydrocarbon burning in the methane coupling process into the cracking process stream. Such components require an expensive separation from the hydrocarbons downstream in the IFP process.

More recently U.S. Pat. No. 5,118,898 has taught a process for producing ethylene from a methane rich gas stream and an ethane rich gas stream by (i) introducing the methane rich gas stream and molecular oxygen into a lower zone of a fluidized bed of particles which are catalytically active in promoting an exothermic oxidative coupling reaction to product ethylene and other hydrocarbons, (ii) subjecting the effluent from (i) to an endothermic pyrolysis reaction in an upper zone of the same fluidized bed of catalytic particles to produce further ethylene and other olefinically unsaturated hydrocarbons. Use of a single fluidized bed has several drawbacks, however, including importantly back mixing of the catalytic particles and hydrocarbon components produced in the upper into the lower zone of the fluidized bed containing molecular oxygen. While circulation of the fluidized bed of particles within the reactor is able to transfer exothermic heat from the oxidative coupling zone to the pyrolysis zone of the fluidized bed, both of the steps (i) and (ii) must occur at substantially the same temperature.

SUMMARY OF INVENTION

In broad aspect, the invention is an apparatus using integrated catalytic heat-transfer walls for simultaneously coupling of methane and dehydrogenating of saturated hydrocarbon compounds in a separate gas. The apparatus comprises either an array of tubes containing channels for flow of one gas stream positioned in another gas stream or a core containing channels for separate flow of a first feed which is essentially methane and the oxygen-affording gas and a second feed which contains predominantly saturated hydrocarbons. Each channel has a catalytic heat-transfer wall disposed between the channel and a portion of the outer surface of the tube contacting the gas stem in the passageways, or a common catalytic heat-transfer wall with adjacent core channels. The catalytic heat-transfer wall comprising a gas-impervious material and a suitable catalyst allowing oxidative coupling of methane into higher hydrocarbons.

Using apparatus of the invention for simultaneously coupling of methane and dehydrogenating of saturated hydrocarbon compounds in a separate gas now provides a way to produce olefins in a process not having many of the past disincentives. The process integrates the production of the olefins by hydrocarbon cracking with the methane coupling in a manner in which the individual processes synergistically fit together. Realized objectives of the new process are:

1. Thermal integration of the endothermic olefin cracking process with the exothermic methane coupling process;
2. Thermal integration of the refrigeration processes for enriched or purified oxygen production, olefins recovery, and optionally, natural gas liquids processing;
3. High overall yield of olefins and other products with near complete feed stock utilization; and
4. Substantial reduction of $NO_x$ as a result of process heat being generated by the coupling of methane with oxygen rather than the combustion of fuel with air.

Suitable catalysts allowing oxidative coupling of methane include catalyst comprising at least one element selected from the group consisting of Group IIA and Group IIIA of the periodic table of elements, preferably, at least one oxidized metal selected from the group consisting of magnesium, calcium, strontium, barium, scandium, yttrium, lanthanum, and scandium. Preferred catalysts comprise a combination of at least one oxidized Group IIIA metal, and at least one oxidized Group IIA metal. More preferred are catalysts which further comprises a cationic species of at least one element selected from the group consisting of aluminum, germanium, tin, and lead. Halides may also be present in useful catalyst compositions.

In one aspect, the invention is a dual-flow chemical reactor for simultaneous oxidative coupling of methane using an oxygen-affording gas and cracking-dehydrogenating reactions of organic compounds in a separate gas. In one embodiment of the invention, the dual-flow chemical reactor comprises a vessel having an entrance port, an exit port, and a passageway therebetween for stream flow of one or more gases from the entrance port to the exit port defining a direction of stream flow. Preferably, the direction of stream flow and the direction of channel flow are substantially transverse to one another. At least one reactor core, positioned within the vessel, comprises an array of tubes having an outer surface including a generally flat entrance surface and a generally flat exit surface spaced apart from the entrance surface, and a plurality of tube channels therebetween for flow of one or more gases from the entrance surface to the exit surface operable to define a direction of channel flow. Each channel has a catalytic heat-transfer wall disposed between the channel and a portion of the outer surface of the tubes contacting the gas stream in the passageway. The reactor core further comprises an entrance manifold means in flow communication with channels at the entrance surface of at least one array and an exit manifold means in flow communication with the same channels at one or more exit surface and thereby in flow communication with entrance manifold means. The vessel and the reactor core together form a first zone for introducing, reacting at least one compound therein, and expelling a first gas or gas mixture and wherein the entrance manifold means, the tube channels and the exit manifold means form a second zone within the dual-flow chemical reactor for introducing, reacting at least one compound therein, and expelling a second gas or gas mixture.

In another aspect, the invention is a dual-flow core for simultaneous coupling of methane using an oxygen-affording gas and dehydrogenating of saturated hydrocarbon compounds in separate gas which comprises a ceramic core having a generally flat first entrance surface, a generally flat first exit surface spaced apart from and substantially parallel to the first entrance surface, and a first plurality of core channels therebetween for flow of a first feed which is essentially methane and the oxygen-affording gas from the first entrance surface to the first exit surface operable to define a first direction of channel flow. The ceramic core also having a generally flat second entrance surface, a generally flat second exit surface spaced apart from and substantially parallel to the second entrance surface, and a second plurality of core channels therebetween for flow of a second feed which contains predominantly saturated hydrocarbons, from the second entrance surface to the second exit surface operable to define a second direction of channel flow. Each channel has a portion of channel wall disposed between the oxygen-containing gas stream and the other gas stream comprising a gas-impervious material and a suitable catalyst allowing oxidative coupling of methane into higher hydrocarbons.

In yet another aspect, the invention is a dual-flow chemical reactor for simultaneous coupling of methane using an oxygen-affording gas and dehydrogenating of saturated hydrocarbon compounds in another gas which comprises at least one ceramic core having a generally flat first entrance surface, a generally flat first exit surface spaced apart from and substantially parallel to the first entrance surface, and a first plurality of core channels therebetween for flow of a first feed which is essentially methane and the oxygen-affording gas from the first entrance surface to the first exit surface operable to define a first direction of channel flow. The ceramic core also having a generally flat second entrance surface, a generally flat second exit surface spaced apart from and substantially parallel to the second entrance surface, and a second plurality of core channels therebetween for flow of a second feed which contains predominantly saturated hydrocarbons, from the second entrance surface to the second exit surface operable to define a second direction of channel flow. Each channel has a portion of channel wall disposed between the oxygen-containing gas stream and the other gas stream comprising a gas-impervious material and a suitable catalyst allowing oxidative coupling of methane into higher hydrocarbons. The reactor further comprising a first entrance manifold means in flow communication with first plurality of core channels at the first entrance surface and a first exit manifold means in flow communication with the same channels at the first exit surface, thereby in flow communication with first entrance manifold means, and a second entrance manifold means in flow communication with second plurality of core channels at the second entrance surface and a second exit manifold means in flow communication with the same channels at the second exit surface, thereby in flow communication with second entrance manifold means. The first entrance manifold means, plurality of core channels and exit manifold means together form a first zone for introducing, reacting at least one compound therein and expelling a first gas or gas mixture and the second entrance manifold means, plurality of core channels and exit manifold means together form a second zone for introducing, reacting at least one compound therein and expelling a second gas or gas mixture.

In another aspect, the invention is a integrated chemical conversion process to make olefins which combines coupling of methane and cracking of hydrocarbon compounds in separate gas streams which comprises the steps of (A) providing at least one dual-flow chemical reactor described above, (B) introducing a first feed stream which is essentially methane and an oxygen-affording gas into either the first or second zone, coupling the first feed to produce a product containing $C_2$ hydrocarbons and effectively transferring heat evolved by coupling through the catalytic heat-transfer wall into the other zone, and expelling a residue of the first feed stream, (C) introducing a second feed stream which contains predominantly saturated hydrocarbons into the other zone, cracking at least one of the saturated hydrocarbons using heat evolved by coupling from the first zone to provide a majority of the heat required by the cracking to form primarily an olefin-containing product, and expelling a product-containing gas mixture, and (D) combining the $C_2+$ containing portions of the effluents from the first zone and the second zone and individually separating the methane and at least the ethylene and propylene olefinic hydrocarbon components thereof.

In preferred embodiment of a process according to the invention, the process includes a step (E) returning unreacted methane contained in the effluent of the first zone together with methane contained in the effluent of the second zone to the first feed stream.

In processes according to the invention, it is preferred to have the catalytic coupling of methane reaction and the hydrocarbon cracking reaction are separated by a thermally conductive catalytic heat-transfer wall which is in good thermal contact with both of these reactions.

In another preferred embodiment of a process according to the invention, the hydrocarbons contained in the second feed stream are thermally cracked in the presence of a fluidized bed of particulate solids in the first zone, and/or wherein the coupling is catalytic.

In another preferred embodiment of a process according to the invention, the hydrocarbons contained in the second feed stream are thermally cracked with or without the presence of steam, the coupling is catalytic, and/or wherein separating methane and at least the ethylene and propylene components thereof is carried out cryogenically using hydrocarbons and nitrogen as refrigerants.

In still another preferred embodiment of a process according to the invention, the oxygen-affording gas is essentially oxygen separated from air by liquefaction and fractionation to obtain an essentially oxygen fraction and an essentially nitrogen fraction, and wherein the nitrogen fraction is used to liquefy one or more methane, ethylene and propylene, each under moderate pressure, to provide one or more cryogenic liquids used to effect the cryogenic separation of the olefinic hydrocarbon components.

BRIEF DESCRIPTION OF THE DRAWINGS

The appended claims set forth those novel features which characterize the present invention. The present invention itself, as well as advantages thereof, may best be understood, however, by reference to the following brief description of preferred embodiments taken in conjunction with the annexed drawings, in which:

BRIEF DESCRIPTION OF THE INVENTION

Figure 1:
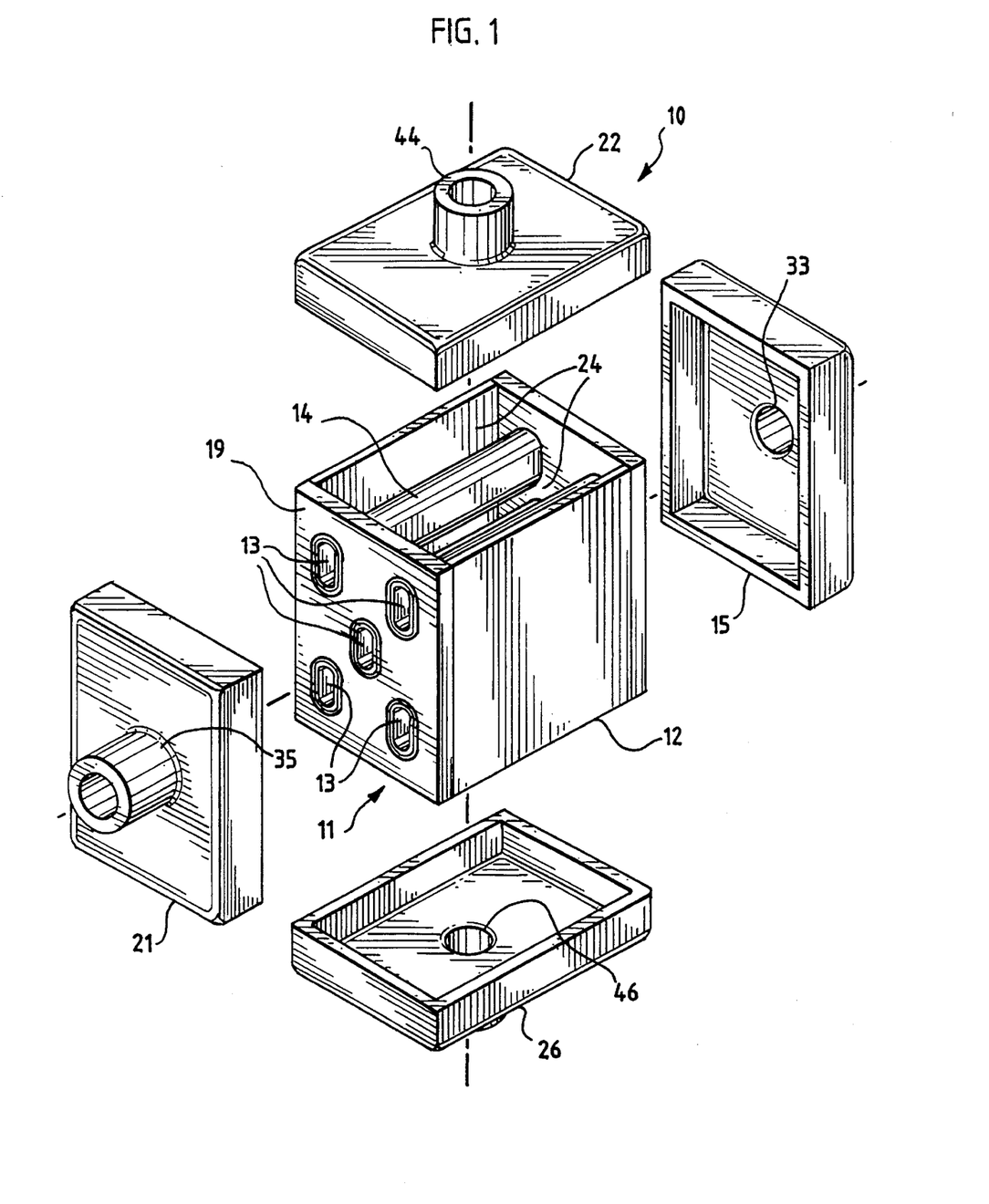
FIG. 1 is an exploded perspective view of one embodiment of a dual-flow reactor in accordance with the present invention.
Figure 2:
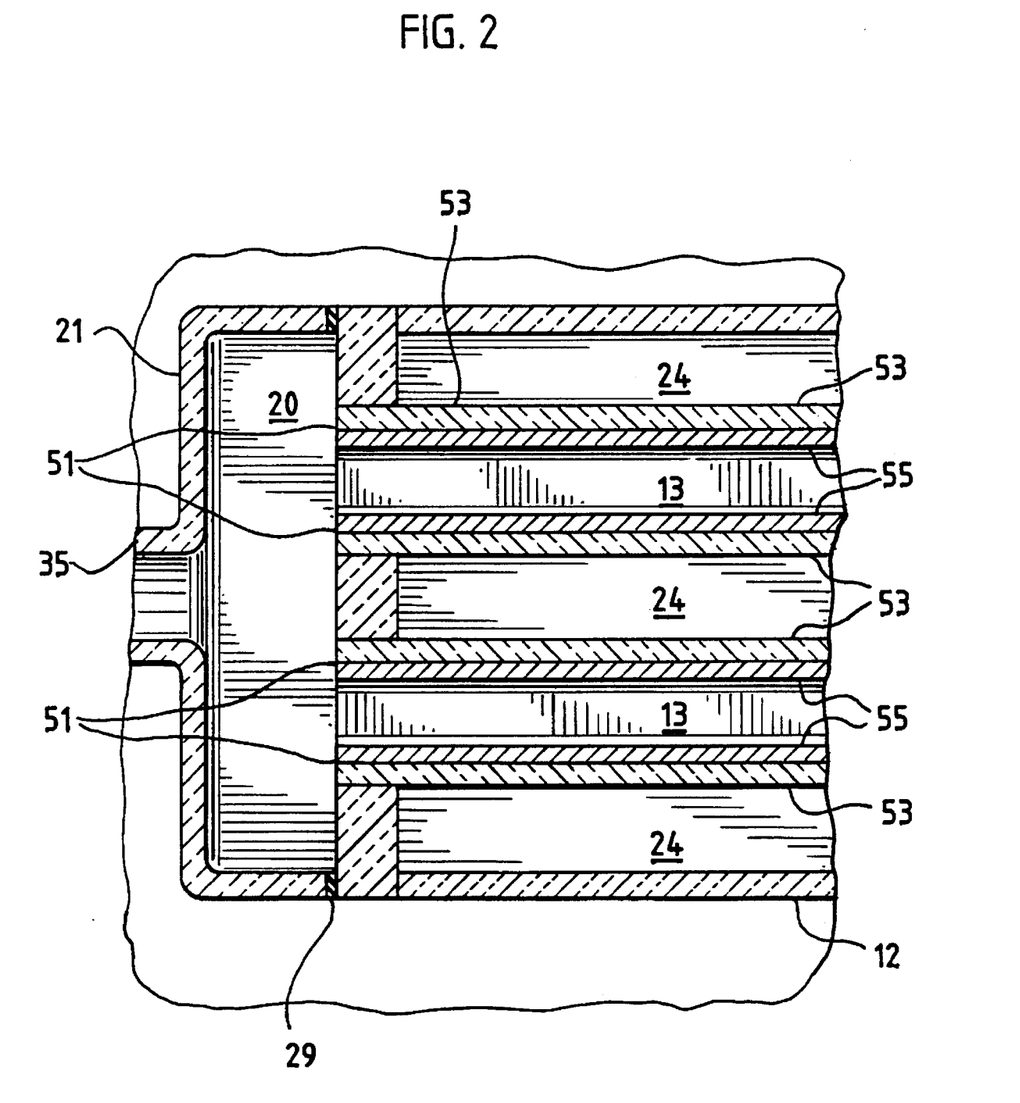
FIG. 2 is a sectional view of the dual-flow reactor of FIG. 1.

FIGS. 1 and 2 illustrate a dual-flow reactor 10 having a reactor core 11 containing an array of five tubes 14 which are positioned across passageways 24 for flow of a gas stream. The reactor core 11 has opposite outer side walls 12 which are generally flat and approximately 90° from an entrance surface for flow through the core and an opposite side exit surface spaced apart from and substantially parallel with each other. The array of reactor tubes together is approximately a rectangular parallelepiped shape. The reactor core 11 has a plurality of tube channels 13 between the entrance surface (not shown) of an entrance and exit surface 19 manifold tube sheet for flow of gases from entrance surface to opposite exit surface and defining a direction of channel flow which is rotated approximately 90° from the entrance and exit surfaces and is approximately 90° from the direction of stream flow through the core. Each channel 13 has a catalytic heat-transfer wall disposed between the channel and a portion of outer tube surface exposed to gas stream. Structures 15 and 21 adjacent opposite entrance and exit surfaces of the reactor core 11 define spaced entrance manifold (not shown) and opposite exit manifold 20 that communicate with one another via channels 13 formed in the tubes. Further, structures 22 and 26 adjacent opposite top and bottom outer surfaces of the reactor core 11 define spaced entrance and exit manifolds (not shown) that communicate with one another via passageways 24 formed by spaces between outer surfaces of the core tubes and wall structures 12. An inlet line 33 in structure 15 is adapted to carry either an organic compound in an oxygen-affording gas stream or another gas stream containing reactants comprising one or more organic compounds to the entrance manifold for flow through channels 13, and an outlet line 35 in structure 21 is adapted to carry a residue of the oxygen-affording gas stream or all remaining gas, unconsumed reactants, and product-containing gas mixture from the exit manifold. Likewise, inlet line 44 in structure 22 is adapted to carry either an organic compound in an oxygen-affording gas stream or another gas stream containing reactants comprising one or more organic compounds to the entrance manifold for flow through passageways 24, and an outlet line 46 in structure 26 is adapted to carry a residue of the oxygen-containing gas stream or all remaining gas, unconsumed reactants, and product-containing gas mixture from the exit manifold. Passageways 24 and channels 13 are disposed transverse to one another, so that the respective inlet and outlet manifolds for an organic compound in an oxygen-containing gas stream and for the another gas stream containing reactants are located alternately adjacent one another.

FIG. 2 illustrates an enlarged cross section of reactor core 11 for dual-flow reactor 10 of FIG. 1. Channels 13, specifically shown for a gas stream of an organic compound in an oxygen-affording gas, are illustrated to extend in the plane of the viewing paper and are formed by catalytic heat-transfer walls 51 comprising a gas-impervious material 53 supporting a suitable catalyst 55 which together form a thermally conductive wall; while the passageways 24 for flow of a gas stream containing reactants comprising one or more organic compounds are illustrated to extend normal to the viewing paper and are formed by spaces between exposed wall surfaces of the reactor core tubes and side structures 12 defining the of passageways 24.

The reactor core 11, and manifold structures 15, 21, 22, and 26 are snugged or otherwise connected together and may be fit within a housing (not shown) and/or have insulation surrounding these components. Also, the annular space between the core, and separate manifold structures can be packed or filled as at 29 with a seal to minimize leakage of gases between the manifolds.

Figure 3:
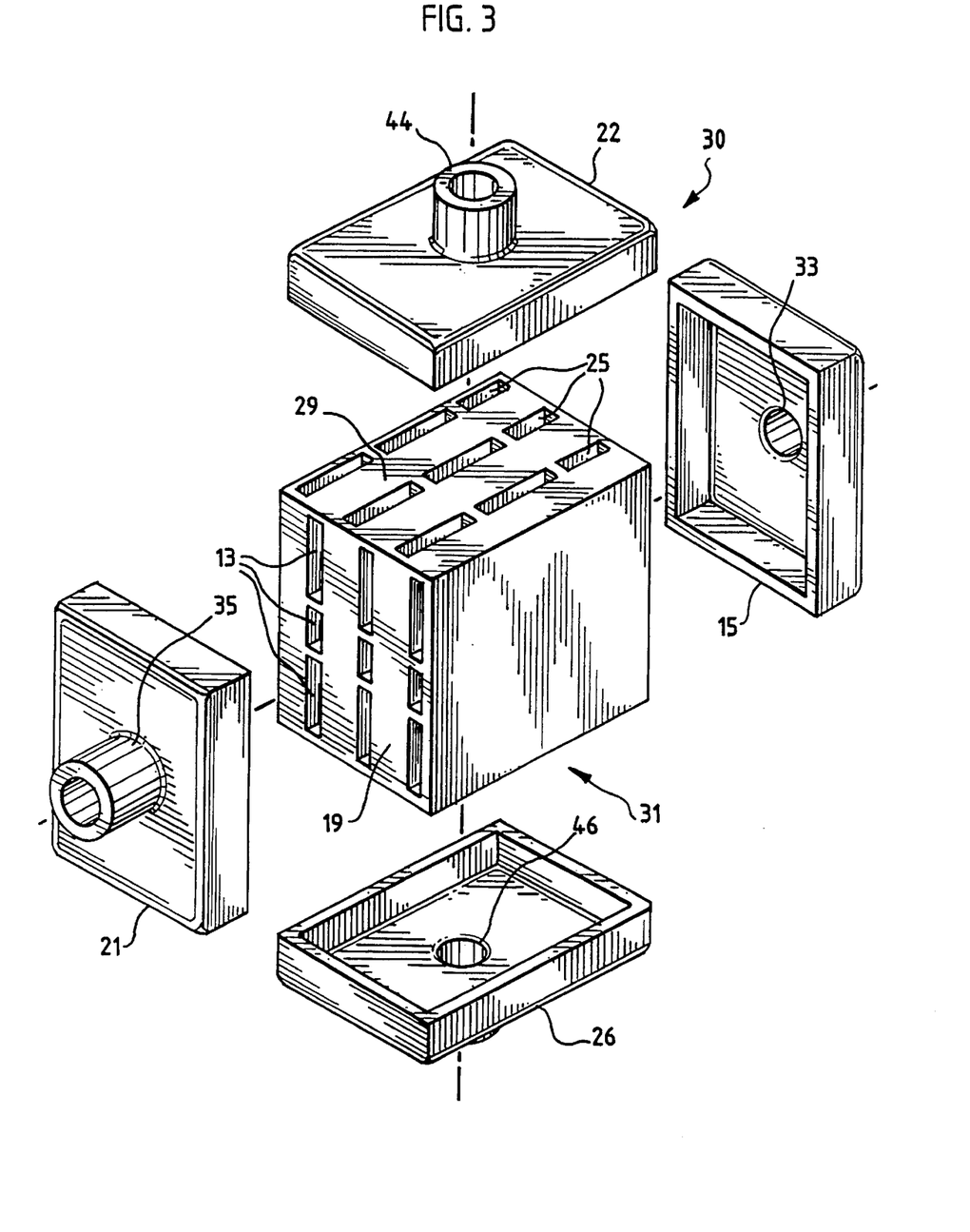
FIG. 3 is an exploded perspective view of another embodiment of a dual-flow reactor in accordance with the present invention.

FIG. 3 illustrates a dual-flow reactor 30 having a reactor core 31 of monolithic construction. The monolithic core is approximately a rectangular parallelepiped shape having two sets of entrance and opposite side exit surfaces, each set spaced apart from and substantially parallel with each other, and top and bottom outer surfaces which are generally flat and approximately 90° from the entrance and exit surfaces. Structures 15 and 21 adjacent opposite entrance surface (not shown) and exit surface 19 of reactor core define spaced entrance and exit manifolds (not shown) that communicate with one another via channels 13 formed in the core. Further, structures 22 and 26 adjacent opposite exit surface 29 and entrance surface (not shown) of reactor core define spaced entrance and exit manifolds (not shown) that communicate with one another via channels 25 formed in the core. An inlet line 33 in structure 15 is adapted to carry either an organic compound in an oxygen-affording gas stream or another gas stream containing reactants comprising one or more organic compounds to the entrance manifold for flow through channels 13, and an outlet line 35 in structure 21 is adapted to carry a residue of the oxygen-affording gas stream or all remaining gas, unconsumed reactants, and product-containing gas mixture from the exit manifold. Likewise, inlet line 46 in structure 26 is adapted to carry either an oxygen-affording gas stream or another gas stream containing reactants comprising one or more organic compounds to the entrance manifold for flow through channels 25, and an outlet line 44 in structure 22 is adapted to carry a residue of the oxygen-containing gas stream or all remaining gas, unconsumed reactants, and product-containing gas mixture from the exit manifold. Channels 13 and channels 25 are disposed transverse to one another, so that the respective inlet and outlet manifolds for oxygen-affording gas stream and for the another gas stream containing reactants are located alternately adjacent one another. The reactor core 31 and manifold structures 15, 21, 22, and 26 are snugged or otherwise connected together and may be fit within a housing (not shown) and/or have insulation surrounding these components. Also, the annular space between the top core, bottom structure, and separate manifold structures can be packed or filled with a ceramic paste or the like seal to minimize leakage of gases between the manifolds.

Figure 4:
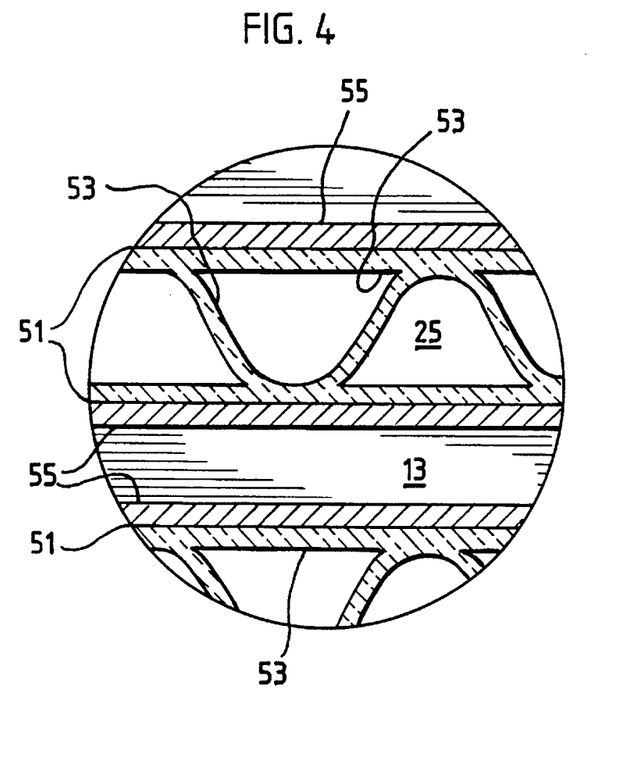
FIG. 4 is a sectional view of a dual-flow core in accordance with the present invention.

FIG. 4 illustrates an enlarged cross section of a ceramic reactor core 31 for dual-flow reactor 30 of FIG. 3. Channels 13, specifically shown for a gas stream of an organic compound in an oxygen-affording gas, are illustrated to extend in the plane of the viewing paper and are formed by catalytic heat-transfer walls 51 comprising a gas-impervious material 53 supporting a suitable catalyst 55 which together form a thermally conductive wall; while the passageways 25 for flow of a gas stream containing reactants comprising one or more organic compounds are illustrated to extend normal to the viewing paper and are formed in the gas-impervious material 53.

It will be appreciated that in dual-flow reactor 10 having an array of reactor tubes 11, the passageways 24 and channels 13 are laid out in a crosswise pattern so that the two gas streams flow transverse to one another, and in dual-flow reactor 30 having a monolithic core of reactor cells 31, the channels 25 and channels 13 are laid out in a crosswise pattern so that the two gas streams flow transverse to one another. These cross flow arrangements allow for direct and efficient manifolding of the opposite open ends of the flow channels and/or passageways, and the manifolds can be extended over almost the entire opposite entrance and exit surfaces or edges of the cores.

Figure 5:
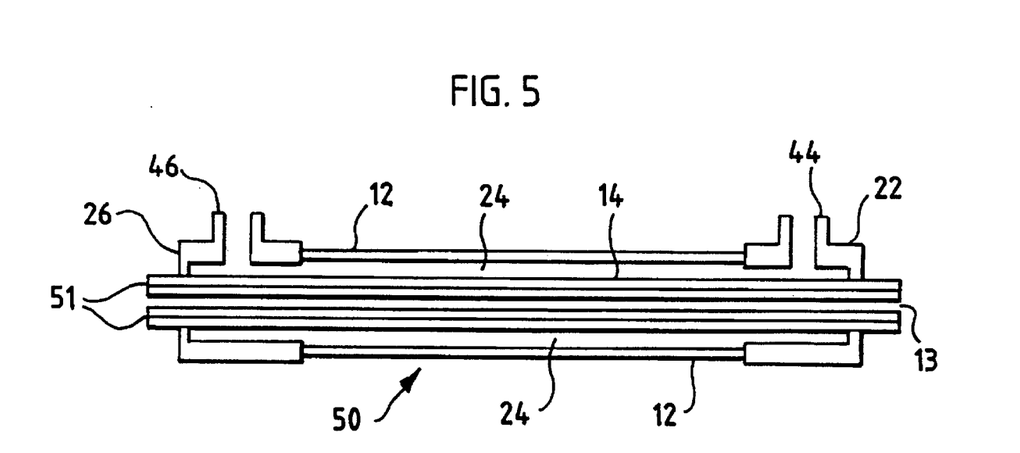
FIG. 5 is a side view and cross-sectional view of yet another embodiment of a dual-flow core in accordance with the present invention.

Another embodiment of dual-flow reactor of the present invention may be schematically represented as shown in FIG. 5 wherein the side view and cross-section of the dual-flow reactor 50 shows passageway 24 separated from channel 13 by catalytic heat-transfer walls 51 comprising a gas-impervious material supporting a suitable catalyst. Passageway 24 for flow of a gas stream is defined by outer surface 14 of heat-transfer walls 51 and side structures 12. The array of reactor tubes together is approximately a rectangular parallelepiped shape. Tube channel 13 for flow of gases from entrance surface to opposite exit surface defines a direction of channel flow which is substantially parallel with the direction of stream flow through passageway 24. Structures (not shown) adjacent opposite entrance and exit surfaces of channel 13 define spaced entrance manifold (not shown) and opposite exit manifold 20 (not shown) that communicate with one another via channels 13. Further, structures 22 and 26 define spaced entrance and exit manifolds (not shown) that communicate with one another via passageways 24 formed by spaces between outer surfaces of heat-transfer walls 51 and wall structures 12. An inlet line is adapted to carry either an organic compound in an oxygen-affording gas stream or another gas stream containing reactants comprising one or more organic compounds to the entrance manifold for flow through channels 13, and an outlet line is adapted to carry a residue of the oxygen-affording gas stream or all remaining gas, unconsumed reactants, and product-containing gas mixture from the exit manifold. Likewise, inlet line 44 in structure 22 is adapted to carry either an organic compound in an oxygen-affording gas stream or another gas stream containing reactants comprising one or more organic compounds to the entrance manifold for flow through passageways 24, and an outlet line 46 in structure 26 is adapted to carry a residue of the oxygen-containing gas stream or all remaining gas, unconsumed reactants, and product-containing gas mixture from the exit manifold. Passageways 24 and channel 13 are disposed substantially parallel to one another, so that the respective directions of gas flow form inlet and outlet manifolds for an organic compound in an oxygen-affording gas stream and for the another gas stream containing reactants may be co-current or counter-current to one another as desired.

The catalytic coupling of methane is, typically, carried out using a feed that is essentially methane which can be pure methane or methane containing various small amounts of other materials. Natural gas, which is mainly methane, or other light hydrocarbon mixtures which are readily available, inexpensive, are particularly preferred feed materials for processes of this invention. The natural gas can be either wellhead natural gas or processed natural gas. Composition of processed natural gas varies with the needs of the ultimate user. A typical processed natural gas composition contains about 70 percent by weight of methane, about 10 percent by weight of ethane, 10 percent to 15 percent of $CO_2$, and the balance is made up of smaller amounts of propane, butane and nitrogen. The feed to the methane coupling reactor, preferably, should not contain substantial amounts of $C_2+$ hydrocarbons as they are preferentially oxidatively dehydrogenated by the oxygen present in the coupling process at the expense of methane and also produce undesired water as a product. Natural gas containing $C_2+$ hydrocarbons can be used as a feed to the catalytic methane coupling unit after first separating the $C_2+$ hydrocarbons, for example, by first passing the natural gas through the demethanizer.

A large number of catalysts or agents are able to carry out methane coupling and a considerable number are recorded in the public literature. See, for example, U.S. Pat. No. 4,939,311 issued Jul. 3, 1990, in the name of Washecheck et al., U.S. Pat. No. 4,971,940 issued Nov. 20, 1990, in the name of Kaminsky et al., U.S. Pat. No. 5,024,908 issued Jun. 18, 1991, in the name of Karninsky et al., U.S. Pat. No. 5,059,740 issued Oct. 22, 1991, in the name of Kaminsky et al., U.S. Pat. No. 5,196,634 issued Mar. 23, 1993, in the name of Washecheck et al., and U.S. Pat. No. 5,198,596 issued Mar. 30, 1993, in the name of Kaminsky et al. The specifications and claims of each of these commonly assigned U.S. patents are incorporated by reference herein.

Catalysts or agents useful in the methane coupling reaction are generally heavy metal oxides, binary metal oxides and ternary metal oxides. Preferably, the metals used are those whose oxides are not volatile under the high temperature used in the methane coupling reaction. Metal oxides and metal oxide systems such as lead oxide, YBaZr oxide, SrLa oxide etc. may be used. It is preferable that the catalyst or agent used is one which has a high activity, conversion, and selectivity to $C_2$ hydrocarbons, particularly to ethylene, as can be understood by one skilled in the art.

Methane coupling is carried out over the catalyst or agent in the presence of an oxygen-affording gas such as air, oxygen-enriched air and oxygen, preferably oxygen, at pressures, temperatures and space velocities that are well known to those skilled in the art. Generally, the oxygen to methane ratio used is less than 1:1 so that the oxygen is completely converted in the coupling reaction and unreacted methane recycled to the methane coupling feed after separation of the methane coupling products. The product of methane coupling is largely the $C_2$ hydrocarbons, ethane and ethylene, with ethylene the most desired product. However, substantial amounts of carbon oxides and water as well as smaller amounts of $C_3+$ hydrocarbons can be formed as can be understood by one skilled in the art.

One or more zones of the dual-flow reactor can contain a fixed bed, a moving bed, or a fluidized bed of particulate solids although a fluidized bed reactor may be preferred from the point of view of heat transfer. The partial oxidation catalyst or agent is, in a favored embodiment, adhered to the walls in the form of a skin on the reactor tube to facilitate transport of heat across the reactor wall. The exothermic methane coupling process and the endothermic hydrocarbon cracking process are carried out in the same reactor separated by a thermally conducting wall between the reaction zones. Preferably, a majority of the heat required in the endothermic cracking process is supplied by the heat evolved in the methane coupling process. More preferably, over 70% of the heat is supplied by methane coupling. The heat supplied by methane coupling is produced less pollutively than by burning, for example, methane with air as the amount of $NO_x$ is reduced to almost zero.

Instead of introducing feed air to the liquid air plant at ambient temperature, advantage can be taken of the existing refrigeration unit present in the usual olefins plant. In this embodiment, feed air is first cooled in stages in the propylene refrigeration unit and then further cooled in the ethylene refrigeration unit. It may be fed then to the liquid air plant at temperatures down to $-150°$ F. at 16 psia.

Hydrocarbon cracking is carried out using a feed which is ethane, propane or a hydrocarbon liquid ranging in boiling point from light straight run gasoline through gas oil. Ethane, propane or mixtures thereof is the preferred feed to a hydrocarbon cracking unit. Generally, hydrocarbon cracking is carried out thermally in the presence of dilution stem in large cracking furnaces which are heated by burning at least in part methane and other waste gases from the olefins process resulting in large amounts of $NO_x$ pollutants. The hydrocarbon cracking process is very endothermic and requires large quantities of heat per pound of product. However, newer methods of processing hydrocarbons utilizes at least to some extent catalytic processes which are better able to be tuned to produce a particular product slate. The amount of stem used per pound of feed in the thermal process depends to some extent on the feed used and the product slate desired. Generally, stem pressures are in the range of about 30 $lb/in^2$ to about 80 $lb/in^2$, and amounts of stem used are in the range of about 0.2 lb of stem per lb of feed to 0.7 lb of stem per lb of feed. The temperature, pressure and space velocity ranges used in thermal hydrocarbon cracking processes to some extent depend upon the feed used and the product slate desired, which are well known as may be appreciated by one skilled in the art.

The following Examples will serve to illustrate certain specific embodiments of the herein disclosed invention. These Examples should not, however, be construed as limiting the scope of the novel invention as there are many variations which may be made thereon without departing from the spirit of the disclosed invention, as those of skill in the art will recognize.

EXAMPLES

In the following Examples catalytic heat-transfer walls which have both gas-impervious materials and suitable catalysts allowing oxidative coupling of methane into higher hydrocarbons were prepared as follows.

Example 1

1% $Sr/La_2O_3$ coated Ni Tube

A pure nickel tube (⅜" O.D., 0.035" wall, 1.25" long) was roughened using sandpaper and then cleaned using acetone. A gray homogenized slurry of ceramic adhesive was prepared by first mixing 8.0 g of a commercial $MgO/Al_2O_3$ powder (CERAMABOND™ 571 from Aremco Products, Inc., Ossiing, N.Y.) with 5.33 g of liquid sodium silicate in a vial. The roughened tube was dipped into the gray homogenized slurry so that the entire inside and outside surface of the tube was coated. The tube was allowed to air dry overnight and then cured by heating in air according to the following temperature program: Heat at 5° C./min to 93° C., hold for 2 hours, heat at 2 C./min to 371° C., hold for 1 hour, cool to room temperature. The coated tube was then subjected to oxidative coupling conditions at temperatures from 600° C. to 850° C. This caused the coating to become more of an off white, tan color.

A catalyst, identified as 1% $Sr/La_2O_3$, was prepared by dissolving $Sr(NO_3)_2$, (0.48579 g, 0.002295 moles) into 20 mL of deionized water and to this solution $La_2O_3$ (20.0 g, 0.06138 moles) powder was added while mixing to form a paste.

The coated tube was then rolled in this paste such that a certain amount of the paste adhered to the tube. The coated tube was then calcination according to the following temperature program: Heat at 2° C./min to 400° C., hold for 1 hour, heat at 2° C./min to 850° C., hold for 8 hours, the cool to room temperature. The off white $Sr/La_2O_3$ was adhered to the walls of the tube after this treatment.

Example 2

1% $Sr/La_2O_3$ coated Ni Tube

Preparation of catalytic heat-transfer walls according to Example 1 was repeated in several modifications as described in this example. Both a nickel tube and a Incoloy-600 tube were coated with a ceramic adhesive in a manner similar to that described in Example 1. A $Sr/La_2O_3$ solution was prepared by dissolving $Sr(NO_3)_2$ (0.024 g, $1.15 \times 10^{-4}$ moles) and $La(NO_3)_3 \cdot 6H_2O$ (5.0 g, 0.0115 moles) in 10 mL of acetone mixed with 3 mL of deionized water. The nitrates were dissolved by gently heating the mixture which also evaporated some of the acetone and caused the viscosity of the liquid to increase. The coated tubes which had been cured to 371° C. were dipped into this solution and then dried at 120° C. in a vacuum oven for 30 minutes. The tubes were again dipped into the solution and dried to increase the coating thickness. The coated tubes were then calcined to 850° C. for 8 hours.

Example 3

$Y_1Ba_2Zr_3O_y$ coated Ni Tube

A catalyst with nominal composition $Y_1Ba_2Zr_3O_y$ was prepared by heating $Ba(OH)_2 \cdot 8H_2O$ (25 g, 0.0792 moles) in a 3-necked flask under a nitrogen purge until it melted at temperatures form about 85° C. to about 90° C. $Y(NO_3)_2 \cdot 6H_2O$ and $ZrO(NO_3)_2 \cdot xH_2O$ were added to this melt with stirring to form the desired solution. The resulting liquid was allowed to cool and then was transferred as a solid to a $Y(ZrO_2)$ crucible where it was calcined to 850° C. for 8 hours. The calcined powder (1.54 g) was then mixed with 6.00 g of $MgO/Al_2O_3$ powder. To this mixture 6.06 g of liquid sodium silicate was added and mixed to a paste consistency. A pure nickel tube was coated with this mixture and followed by curing and calcination as described in Example 1.

Example 4

$Y_1Ba_2Zr_3O_y$ Coated Ni Tube

The $Y_1Ba_2Zr_3O_y$ catalyst describe in Example 3 (4.3 g) was ground to a fine powder and mixed with liquid sodium silicate (3.6 g). The resulting paste was then used to coat another pure nickel tube of the same size as described in Example 1. A thick coating adhered to the tube which was then air dried and cured as described in Example 1. The final calcination was done in air at 850° C. for 8 hours.

Example 5

$Y_1Ba_2Zr_3O_y$ coated Ni Tube

A ceramic adhesive was prepared by mixing $MgO/Al_2O_3$ powder (6.0 g) with liquid sodium silicate (6.0 g) in air forming a paste. A pure nickel tube was then dipped into this paste so that a uniform coating covered the inside and outside of the tube. The calcined $Y_1Ba_2Zr_3O_y$ (2.0 g of 60/80 powder) was then sprinkled onto the wet coating and allowed to air dry. The coated tube was then cured and calcined as described in Example 1.

Example 6 and Comparative Example A

Catalyst coated tubes were screened for catalytic activity using a three zone electric tube furnace micro reactor. The ⅜" O.D., 1.25" long coated tubes were placed into a 14 mm I.D. quartz reactor tube. The coated tube replaced a conventional packed bed of comparable catalyst. A quartz thermocouple well was placed up the middle of the coated tube which was held in the middle of the reactor tube with a quartz wool plug and a quartz deadman. The feed was 30% $CH_4$, 6% $O_2$ and the balance $N_2$. The results for the 13702-125-1 $Sr/La_2O_3$ coated Ni tube are shown in Table 1. At 850° C. at least 61% $C_2+$ selectivity and 97% oxygen conversion was observed at 350 sccm of feed. Results shown for Comparative Example A in Table 1 under heading Conventional Packed Bed were obtained using 1% $Sr/La2O3$ by diluting catalyst 39 to 1 with $\alpha$ $Al_2O_3$ particles.

Example 7 and Comparative Example B

The screening for catalytic activity described for Example 6 and Comparative Example A was repeated in these examples using $Y_1Ba_2Zr_3O_y$ catalyst. Results are shown in Table 2 below. For temperatures at 850° C. and feed flow rate of 152 sccm, total $C_2+$ selectivity was 54% at 95.6% Oxygen conversion.

TABLE 1

| OXIDATIVE COUPLING OF METHANE OVER 1% $Sr/La_2O_3$ | | |
|---|---|---|
| | Conventional Packed Bed | Catalytic Heat-Transfer Wall |
| Temp, °C. | 850 | 843 |
| GHSV, $hr^{-1}$ | 255,000 | 298,800 |
| Conversion of | mole % | mole % |
| Oxygen | 100 | 95 |
| Methane | 22.5 | 23.3 |
| Selectivity to | mole % | mole % |
| $C_2H_4$ | 30.57 | 31.59 |
| $C_2H_6$ | 25.32 | 26.57 |
| $C_2H_2$ | 0.62 | 0.0 |
| $C_3H_8$ | 0.96 | 1.2 |
| $C_3H_6$ | 2.36 | 2.29 |
| Methyl Acetlyene | 0.14 | 0.06 |
| Allene | 0.09 | 0.05 |
| $C_4H_6$ | 0.35 | 0.75 |
| CO | 6.4 | 8.35 |
| $CO_2$ | 33.18 | 29.2 |
| TOTAL TO $C_{2+}$ | 60 | 62 |

TABLE 2

OXIDATIVE COUPLING OF METHANE OVER $Y_1Ba_2Zr_3O_y$

|  | Conventional Packed Bed | Catalytic Heat-Transfer Wall |
|---|---|---|
| Temp, °C. | 850 | 850 |
| GHSV, hr$^{-1}$ | 47,900 | 90,600 |
| Conversion of | mole % | mole % |
| Oxygen | 100 | 95.6 |
| Methane | 25.3 | 19.4 |
| Selectivity to | mole % | mole % |
| $C_2H_4$ | 38.88 | 33.09 |
| $C_2H_6$ | 23.90 | 16.84 |
| $C_2H_2$ | 0.86 | 0.64 |
| $C_3H_8$ | 0.71 | 0.0 |
| $C_3H_6$ | 2.82 | 3.04 |
| Methyl Acetlyene | 0.22 | 0.3 |
| Allene | 0.13 | 0.15 |
| $C_4H_6$ | 0.0 | 0.57 |
| CO | 4.21 | 8.96 |
| $CO_2$ | 27.37 | 36.42 |
| TOTAL TO $C_{2+}$ | 68 | 54 |

That which is claimed is:

1. A process to make olefins which comprises the steps of:

(A) providing a cross-flow chemical reactor fox combined coupling of methane using an oxygen-affording gas and dehydrogenating of saturated hydrocarbon compounds in separated reaction spaces, which reactor comprises; a vessel having an entrance port, an exit port, and a passageway therebetween containing a stream of one or more gases flowing from the entrance port to the exit port operable to define a direction of stream flow, and passageway therebetween containing a stream of one or more gases flowing from the entrance port to the exit port operable to define a direction of stream flow, and at least one reactor core positioned within the vessel comprising an array of tubes having an outer surface including a generally flat entrance surface and a generally flat exit surface spaced apart from and substantially parallel to the entrance surface, and a plurality of tube channels therebetween containing one or more gases flowing from the entrance surface to the exit surface operable to define a direction of channel flow, wherein each channel has a catalytic heat-transfer wall disposed between the channel and a portion of the outer surface of the tubes contacting the gas stream in the passageway, the catalytic heat-transfer wall comprising a ceramic antifoulant coating, a gas-impervious material comprising a high temperature metal or metallic alloy, and, on the portion of the outer surface of the tubes contacting the gas stream in the passageway, a suitable catalyst means for oxidative coupling of methane into higher hydrocarbons, the reactor core further comprising an entrance manifold means in flow communication with channels at the entrance surface of at least one array and an exit manifold means in flow communication with the same channels at one or more exit surface and thereby in flow communication with entrance manifold means, and wherein the entrance port, the passageways, the outer surfaces of the tubes, and the exit port form a first zone for introducing and reacting at least one compound therein, and expelling a first gas or gas mixture and wherein the entrance manifold means, the tube channels and the exit manifold means form a second zone within the dual-flow chemical reactor for introducing, reacting at least one compound therein, and expelling a first gas or gas mixture and wherein the entrance manifold means, the tube channels and the exit manifold means form a second zone within the dual-flow chemical reactor for introducing, reacting at least one compound therein, and expelling a second gas or gas mixture;

(B) introducing a first feed stream which is essentially methane and an oxygen-affording gas into the first zone, coupling the first feed to produce a product containing $C_2$ hydrocarbons and effectively transferring heat evolved by coupling through the catalytic heat-transfer wall into the second zone, and expelling a residue of the first feed stream, (C) introducing a second feed stream which contains predominantly saturated hydrocarbons into the second zone, cracking at least one of the saturated hydrocarbons using heat evolved by coupling from the first zone to provide a majority of the heat required by the cracking to form primarily an olefin-containing product, and expelling a product-containing gas mixture, (D) combining the $C_2$+ containing portions of the effluents from the first zone and the second zone and individually separating the methane and at least the ethylene and propylene olefinic hydrocarbon components thereof, and (E) returning unreacted methane contained in the effluent of the first zone together with methane contained in the effluent of the second zone to the first feed stream.

2. The process of claim 1 wherein the hydrocarbons contained in the second feed stream are thermally cracked in the presence of a fluidized bed of particulate solids in the second zone.

3. The process of claim 1 wherein hydrocarbons contained in the second feed stream are thermally cracked in the presence of steam, and wherein the separating of the methane and at least the ethylene and propylene components is carried out cryogenically using hydrocarbons and nitrogen as refrigerants.

4. The process of claim 3 wherein the oxygen-affording gas is essentially oxygen separated from air by liquefaction and fractionation to obtain an essentially oxygen fraction and an essentially nitrogen fraction, and wherein the nitrogen fraction is used to liquefy one or more methane, ethylene and propylene, each under moderate pressure, to provide one or more cryogenic liquids used to effect the cryogenic separation of the olefinic hydrocarbon components.

5. The process of claim 1 wherein the gas-impervious material comprises nickel or a metallic alloy thereof.

6. The process of claim 5 wherein hydrocarbons contained in the second feed stream are thermally cracked, and wherein the separating the methane and at least the ethylene and propylene components thereof is carried out cryogenically using hydrocarbons and nitrogen as refrigerants.

7. The process of claim 6 wherein said oxygen-affording gas is essentially oxygen which is separated from air by liquefaction and fractionation to obtain an essentially oxygen fraction and an essentially nitrogen fraction, and where the nitrogen fraction is used to liquefy one or more of methane, ethylene and propylene, each under moderate pressure, to provide one or more cryogenic liquids used to effect the cryogenic separation of said olefinic hydrocarbon components.

8. A process to make olefins which combines cracking of a hydrocarbon feedstock with coupling of methane, the process comprising the steps of:

provi ding a combined process reactor suitable for coupling of methane using an oxygen-affording gas and dehydrogenating of saturated hydrocarbon compounds in separated reaction spaces, which reactor comprises;
a first reaction space and
a second reaction space separated from the first reaction space by catalytic thermally conducting tube walls comprising a suitable catalyst means for oxidative coupling of methane into higher hydrocarbons;

coupling in the first reaction space of a first feed stream which is essentially methane using an oxygen-affording gas to produce a product containing $C_2$ hydrocarbons, and transferring heat evolved by coupling through the catalytic heat-transfer wall into the second reaction space;

hydrocarbon cracking in the second reaction space of a second feed stream which contains predominantly saturated hydrocarbons to form primarily an olefin-containing product;

effectively using the heat evolved by coupling in the first space which is transferred through the catalytic heat-transfer wall to provide a majority of the heat required by the cracking without mixing hot effluent of the first reaction space into the second reaction space;

combining the $C_2+$ containing portions of the effluents from the first reaction space and the second reaction space, and individually separating the methane and at least the ethylene and propylene olefinic hydrocarbon components thereof; and returning unreacted methane contained in the effluent of the first reaction space together with methane contained in the effluent of the second reaction space to the first reaction space.

9. The process to make olefins according to claim 8 wherein the catalytic thermally conducting tube walls comprise a ceramic antifoulant coating, the gas-impervious material comprising a high temperature metal or metallic ahoy, and the suitable catalyst means for oxidative coupling of methane into higher hydrocarbons is adhered to the walls in the form of a skin on the reactor tube to facilitate transport of heat across the reactor wall whereby a majority of the heat required in the endothermic cracking process is supplied by the heat evolved in the methane coupling.

10. The process to make olefins according to claim 9 wherein the catalyst means for oxidative coupling of methane comprises at least one oxidized metal selected from the group consisting of scandium, yttrium, lanthanum, magnesium, calcium, strontium, and barium.

11. The process to make olefins according to claim 9 wherein the gas-impervious material comprises nickel or a metallic alloy thereof.

12. The process to make olefins according to claim 9 wherein the catalyst means for oxidative coupling of methane comprises a combination of at least one oxidized Group IIIA metal and at least one oxidized Group IIA metal.

13. The process to make olefins according to claim 9 wherein the oxygen-affording gas is essentially oxygen which is separated from air by liquefaction and fractionation to obtain an essentially oxygen fraction and an essentially nitrogen fraction, and where the nitrogen fraction is used to liquefy one or more of methane, ethylene and propylene, each under moderate pressure, to provide one or more cryogenic liquids used to effect the cryogenic separation of the olefinic hydrocarbon components, and wherein hydrocarbons contained in the second feed stream are thermally cracked.

* * * * *

UNITED STATES PATENT AND TRADEMARK OFFICE
CERTIFICATE OF CORRECTION

PATENT NO. : 5,599,510

DATED : February 4, 1997

INVENTOR(S) : Mark P. Kaminsky, et al

Page 1 of 3

It is certified that error appears in the above-indentified patent and that said Letters Patent is hereby corrected as shown below:

| Col. | Line | |
|---|---|---|
| 1 | 50 | "catalytic heat-transfer wails" should read --catalytic heat-transfer walls-- |
| 4 | 5 | "a stem cracking process" should read --a steam cracking process-- |
| 5 | 13-14 | "the gas stem in the passageways," should read --the gas steam in the passageways,-- |
| 8 | 39 | "of an entrance and exit surface 19 manifold tube sheet" should read --of an entrance manifold tube sheet and exit surface 19 of an exit manifold tube sheet-- |

UNITED STATES PATENT AND TRADEMARK OFFICE
CERTIFICATE OF CORRECTION

PATENT NO. : 5,599,510                                            Page 2 of 3
DATED      : February 4, 1997
INVENTOR(S): Mark P. Kaminsky, et al It is certified that error appears in the above-indentified patent and that said Letters Patent is hereby corrected as shown below:

| Col. | Line |  |
|------|------|--|
| 11 | 33-34 | "U.S. Pat. No. 5,024,908 issued Jun. 18, 1991, in the name of Karninsky et al.," should read --U.S. Pat. No. 5,024,908 issued Jun. 18, 1991, in the name of Kaminsky et al.,-- |
| 12 | 28 | "dilution stem" should read --dilution steam-- |
| 12 | 37 | "The amount of stem used" should read --The amount of steam used-- |
| 12 | 39 | "Generally, stem pressures" should read --Generally, steam pressures-- |
| 12 | 40-41 | "amounts of stem used" should read --amounts of steam used-- |
| 12 | 41 | "0.2 lb of stem" should read --0.2 lb of steam-- |
| 12 | 42 | "0.7 lb of stem" should read --0.7 lb of steam-- |

UNITED STATES PATENT AND TRADEMARK OFFICE
CERTIFICATE OF CORRECTION

PATENT NO. : 5,599,510
DATED : February 4, 1997
INVENTOR(S) : Mark P. Kaminsky, et al It is certified that error appears in the above-indentified patent and that said Letters Patent is hereby corrected as shown below:

| Col. | Line |  |
|------|------|---|
| 14 | 33 | "using 1% Sr/La2O3" should read --using 1% $Sr/La_2O_3$-- |
| 15 | 27 | "a cross-flow chemical reactor fox combined coupling of methane" should read --a cross-flow chemical reactor for combined coupling of methane-- |
| 18 | 4-5 | "metallic ahoy," should read --metallic alloy,-- |

Signed and Sealed this

Twenty-sixth Day of August, 1997

Attest:

BRUCE LEHMAN

Attesting Officer

Commissioner of Patents and Trademarks